United States Patent [19]

Karl et al.

[11] Patent Number: 5,541,117
[45] Date of Patent: Jul. 30, 1996

[54] IMMUNOLOGICAL METHOD FOR THE DETERMINATION OF A HAEMOGLOBIN DERIVATIVE

[75] Inventors: Johann Karl, Peissenberg; Lorenz Kerscher, Penzberg; Erich Schneider, Mannheim, all of Germany

[73] Assignee: Boehringer Mannheim GmbH, Mannheim, Germany

[21] Appl. No.: 26,464

[22] Filed: Mar. 4, 1993

[30] Foreign Application Priority Data

Mar. 5, 1992 [DE] Germany .................. 42 06 932.7

[51] Int. Cl.$^6$ .................. G01N 33/53; G01N 33/543; G01N 33/72

[52] U.S. Cl. .................. 436/518; 436/523; 436/531; 436/532; 436/533; 436/534; 436/66; 436/67; 436/815; 435/7.1; 435/962

[58] Field of Search .................. 436/518, 523, 436/531, 532, 533, 534, 66, 67, 808, 815; 435/7.1, 962

[56] References Cited

U.S. PATENT DOCUMENTS

| | | | |
|---|---|---|---|
| 4,247,533 | 1/1981 | Cerami et al. | 436/542 |
| 4,478,744 | 10/1984 | Mezei et al. | 530/322 |
| 4,647,654 | 3/1987 | Knowles et al. | 530/326 |
| 4,658,022 | 4/1987 | Knowles et al. | 530/402 |
| 4,727,036 | 2/1988 | Knowles et al. | 530/387.9 |
| 4,806,468 | 2/1989 | Wagner et al. | 435/7.1 |
| 4,861,728 | 8/1989 | Wagner | 436/501 |

FOREIGN PATENT DOCUMENTS

| | | |
|---|---|---|
| 185870 | 7/1986 | European Pat. Off. . |
| 201187 | 11/1986 | European Pat. Off. . |
| 215401 | 3/1987 | European Pat. Off. . |
| 309883 | 4/1989 | European Pat. Off. . |
| 315864 | 5/1989 | European Pat. Off. . |
| 407860 | 1/1991 | European Pat. Off. . |
| 184787 | 4/1991 | European Pat. Off. . |
| 444241 | 9/1991 | European Pat. Off. . |
| 2559267 | 9/1985 | France . |

OTHER PUBLICATIONS

Database WPIL Week 8723.
Oshiro et al. "New Method for Hemoglobin Determination by Using Sodium Lauryl Sulfate (SLS)" Clin. Biochem. 15(1) 83–88 (1982).
Harlow et al *Antibodies A Laboratory Manual* Cold Spring Harbor Laboratory (1988) pp. 496, 564–566.

Primary Examiner—Toni R. Scheiner
Assistant Examiner—Lora M. Green
Attorney, Agent, or Firm—Felfe & Lynch

[57] ABSTRACT

The invention concerns a method for the determination of the content of a particular haemoglobin derivative in a blood sample. In particular, the invention concerns a method for the determination of the content of haemoglobin derivatives such as glycated haemoglobin which require the separate determination of the total haemoglobin content and the determination of the haemoglobin derivative in order to determine the proportion of the derivatized haemoglobin in the blood as well as a suitable haemolysis reagent for this.

13 Claims, 7 Drawing Sheets

IMMUNOLOGICAL METHOD FOR THE DETERMINATION OF A HAEMOGLOBIN DERIVATIVE

The invention concerns a method for the determination of the content of a particular hemoglobin derivative in a blood sample. In particular, the present invention concerns a method for the determination of the content of hemoglobin derivatives such as glycated haemoglobin which require the separate determination of the total hemoglobin content and the determination of the hemoglobin derivative in order to determine the proportion of the derivatized hemoglobin in the blood.

Depending on the level of blood sugar, a small amount of the glucose taken up by the erythrocytes binds to the N-terminal valine residue of the β chain of the globin in a non-enzymatic reaction. The reaction to form the stable glycated hemoglobin derivative $HbA_{1c}$ (ketoamine form) proceeds in two steps. Firstly, glucose is bound to hemoglobin via a rapid, reversible attachment with formation of a labile glycated hemoglobin derivative (Schiff base). The stable form is formed by an irreversible slow rearrangement reaction (Amadori rearrangement). The proportion of $HbA_{1c}$ to total hemoglobin is 3–6% in people with healthy metabolism. In patients with diabetes, the proportion of $HbA_{1c}$ can increase in proportion to the level of blood glucose concentration during the previous four to twelve weeks up to values of 12%, occasionally even up to 20%. The determination of the relative proportion of $HbA_{1c}$ to the total hemoglobin content in particular provides an integral parameter to monitor the course of blood sugar control.

A series of methods for the determination of glycated hemoglobin have been described. Conventional methods are based on techniques such as electrophoresis, isoelectric focussing and colorimetric determinations, as well as ion-exchange and affinity chromatography. After the production of specific polyclonal antibodies (U.S. Pat. No. 4,247,533) and monoclonal antibodies (EP-A-0 316 306, EP-A-0 201 187) had been described, a series of immunological methods to detect $HbA_{1c}$ were developed.

EP-A-0 185 870 describes an immunological method for the determination of proteins, including $HbA_{1c}$. Monoclonal antibodies are used which recognize specific linear peptide epitopes. A denaturation is specified for the release of the epitopes, inter alia by means of chaotropic reagents. This denaturation step requires one to several hours at temperatures below 37° C., at temperatures above 50° C. it requires one minute. Simultaneous determination of the total hemoglobin content of the sample is not set forth.

In EP-A-0 201 187 a method for the determination of $HbA_{1c}$ is described in which monoclonal antibodies against $HbA_{1c}$ are used which were obtained by immunization with native human $HbA_{1c}$. The test is carried out at temperatures of 4° to 37° C. whereby each incubation step can take up to 72 hours. A determination of both the total hemoglobin and the $HbA_{1c}$ content in the same sample is not described.

A method is described in EP-A-0 315 864 for the determination of the relative content of $HbA_{1c}$ in a blood sample. Hemoglobin is denatured by thiocyanate and converted into methemoglobin by an additional oxidizing agent preferably ferricyanide. The total hemoglobin content as well as the content of $HbA_{1c}$ can be determined in the blood sample treated in this way.

The use of lithium salts, preferably lithium thiocyanate, to lyse erythrocytes and denature the hemoglobin derivative is described in EP-A-0 407 860. The $HbA_{1c}$ content can be determined immunologically. In order to determine total hemoglobin an oxidizing agent has to be added, preferably ferricyanide, which converts the hemoglobin into methemoglobin.

A disadvantage of the latter two methods is that in order to convert haemoglobin into cyano-methemoglobin, cyanide has to be used. Substitution of cyanide by sodium lauryl-sulfate (SLS) to determine total hemoglobin is described in Clin. Biochem. 15 (1982) 83–88. However, in this reference no indication is given that SLS is suitable for sample pre-treatment in the immunological determination of a hemoglobin derivative, especially of $HbA_{1c}$.

A cyanide-free reagent for the determination of total hemoglobin in a blood sample is also described in EP-A-0 184 787. The reagent is an ionic surface-active agent with a pH of at least 11.3, preferably more than 13.7. The immunological determination of a hemoglobin derivative is not set forth. The very high pH value would be a disadvantage in the immunological determination of a glycated hemoglobin derivative since the sugar moieties can be cleaved from hemoglobin in strongly alkaline media. If the antibody used is labelled with an enzyme, the enzyme reaction could be inhibited since the pH optimum of the enzymes which are usually employed is at a pH of 6 to 8. The immunological reaction may also be inhibited by the high pH value.

There is therefore still a need for an immunological detection method for the determination of a hemoglobin derivative in blood in which the haemolysis can be carried out at low temperatures—such as for example at room temperature—which does not require a long incubation period for the sample preparation and which avoids the use of environmentally harmful reagents such as cyanide. In addition, it should be possible to simultaneously determine total hemoglobin in the same haemolysate in order to be able to determine the proportion of the hemoglobin derivative to the total hemoglobin content of the blood without a further haemolysis preparation. The object of the present invention is to provide such an immunological detection method for the determination of a hemoglobin derivative in blood.

The object is achieved by the invention which is characterized in more detail in the disclosure which follows. This object is essentially achieved by an immunological detection method for the determination of the content of a hemoglobin derivative in a blood sample which is characterized in that the sample is treated with a hemolysis reagent containing an ionic detergent wherein said hemolysis reagent has a pH of from 5 to 9.5 and the hemoglobin derivative is determined immunologically in the hemolyzed blood sample.

The invention also concerns a method for the determination of the content of a hemoglobin derivative and total hemoglobin in a blood sample which comprises treating the blood sample with a hemolysis reagent containing an ionic detergent wherein said hemolysis reagent has a pH of from 5.0 to 9.5, determining the total hemoglobin content in the hemolyzed sample and determining the hemoglobin derivative immunologically in the hemolyzed sample. The total hemoglobin content is preferably determined photometrically.

The invention additionally concerns a hemolysis reagent having a pH of 5 to 9.5, which contains an ionic detergent its use for the sample preparation of a blood sample for the immunological determination of the hemoglobin derivative and, if desired, for the determination of the total hemoglobin content, as well as a test kit containing the hemolysis reagent.

The action of the hemolysis reagent leads to lysis of the erythrocytes present in the blood sample and conversion of hemoglobin into a specific haemoglobin chromophore. The hemoglobin chromophore which is formed can be utilized to determine the total haemoglobin content via its characteristic absorbance and to determine the hemoglobin derivative via the immunological reaction of the specific epitope. In principle, all conventional methods can be used as the immunological method of detection. Direct or indirect (competitive) methods such as e.g. sandwich tests, IEMA tests, precipitation or agglutination tests as well as tests based on the FPIA (fluorescent polarisation immunoassay) and CEDIA$^R$ techniques as well as wet and dry tests are possible. The ionic detergents which can be used in the haemolysis reagent are anionic detergents, preferably sodium dodecylsulfate (SDS), sodium dioctylsulfosuccinate (DONS), cationic detergents, preferably tetradecyltrimethylammonium bromide (TTAB) or cetyltrimethylammonium bromide (CTAB) or zwitterionic detergents, preferably Zwittergent 3-14. The hemolysis reagent is added to the blood sample in an amount which is adequate to lyse the erythrocytes, convert hemoglobin into the specific hemoglobin chromophore and to release the epitopes of the hemoglobin derivative. The hemolysis reagent is added to the blood sample in a ratio of 1:10 to 1:400 so that the concentration of the ionic detergent in the resulting mixture is 0.01 to 5% by weight, preferably 0.5–1.5% by weight. The pH value of the hemolysis reagent is in the weakly acid to weakly alkaline range. The pH is preferably between 5.0 and 9.5, a pH of 7.4 being especially preferred. All conventional buffers can be used to set the pH value in the haemolysis reagent. HEPES, MES, TRIS or phosphate buffer are preferred.

The hemolysis reagent can contain further reagents which for example serve to eliminate interference of the immunological reaction, to oxidize the hemoglobin, to remove turbidity, to stabilize or to preserve. Some detergents, including SDS, can interfere with immunological reactions. In rare cases turbidity and flocculation occurs after addition of the hemolysis reagent which have different causes. For example SDS is poorly soluble at low temperatures. Surprisingly, it turned out that these interferences can be avoided by addition of a non-ionic detergent, preferred detergents are polyoxyethylene ethers such as Brij 35 and 58 or Triton X100 as well as polyoxyethylene esters such as Myrj 52 and 59 or Tween 20. The non-ionic detergent is usually added to the hemolysis reagent in such an amount that, after addition of the sample, the concentration in the resulting mixture is 0.01 to 5% by weight and preferably 0.1–0.5% by weight.

Another commonly used oxidizing agent ferricyanide, for example hexacyanoferrate (III), can be included in the hemolysis reagent. However, in conjunction with cationic detergents precipitation can occur. Furthermore, when ferricyanide is used protection from light is necessary. Surprisingly, it turned out that when preservatives are added whose mechanism of action is based on an oxidative attack of thiol groups, such as for example methylisothiazolone or Bronidox®K, the addition of ferricyanide can be omitted completely. These preservatives in conjunction with cationic detergents result in a brown-green coloured hemoglobin chromophore whose maximum absorbance is at 570 nm. The particular advantage is that firstly the addition of these preservatives leads to a conversion of the hemoglobin into a specific hemoglobin chromophore as well as to a good preservation of the hemolysis reagent and secondly the end point of the hemolysis is readily recognizable by a change in colour from red to brown-green. The preservatives are used in the hemolysis reagent at a concentration of 0.005–0.2% by weight, preferably 0.01–0.02% by weight.

The hemolysis, the conversion of hemoglobin into the specific hemoglobin chromophore as well as the sample preparation to test for hemoglobin derivatives by means of the hemolysis reagent are completed after 1 to 10 minutes at low temperatures, preferably 4° to 37° C. and particularly preferably at room temperature. In most cases an incubation of 2 minutes is sufficient for a complete sample preparation.

The blood sample prepared in this way is subsequently diluted with a reaction buffer in a ratio of 1:10 to 1:100. All current buffers that do not interfere with the immunological reaction can be used as the buffer. MES or HEPES buffer at a concentration of 10 to 200 mmol/l is preferably used. The pH value of the reaction buffer is 5.0 to 8.0. If the immunological test includes an enzyme reaction, the reaction buffer preferably has a pH value which corresponds to the pH optimum of the enzyme reaction. In addition the reaction buffer can already contain the reagents necessary for the hemoglobin derivative test especially the specific binding partners, preferably highly specific polyclonal or monoclonal antibodies.

Surprisingly, it also turned out in this case that the addition of a further detergent, preferably non-ionic detergents such as Brij or Myrj, is advantageous in providing optimal conditions for the sample preparation for detecting the hemoglobin derivative such as glycated hemoglobin as well as for the immunological reaction and avoids interferences. The detergent is added to the reaction buffer in an amount which results in a concentration of 0.01 to 5% by weight, preferably 0.5% by weight in the resulting mixture.

If, in addition to the determination of the hemoglobin derivative, it is intended to determine the total hemoglobin content in the same sample, the absorbance is measured at wavelengths of 400 to 650 nm, preferably 500 to 650 nm and particularly preferably 546 or 570 nm in order to determine the total hemoglobin content preferably after addition of the reaction buffer. In the case of a wet test the absorbance at this wavelength is determined photometrically in a cuvette, in the case of a dry test the absorbance can be determined by reflectance photometry after applying the resulting mixture to a test carrier.

Such a test carrier for the determination of the total hemoglobin content can be constructed very simply since it does not have to contain any chemicals. An absorptive pad which is mounted on a transparent carrier foil is adequate for simple requirements. For the purposes of improved handling and evaluation of the test strip, further carrier layers may be included e.g. a transport pad or a dosage pad.

The total hemoglobin content and the hemoglobin derivative content can also be determined in different portions of the sample after addition of the hemolysis reagent. In this case the total hemoglobin content is determined photometrically in a portion of the mixture of sample and hemolysis reagent, if necessary after appropriate dilution. The reaction buffer is added to the second portion of the mixture and subsequently the hemoglobin derivative is determined immunologically.

In principle all current immunological methods are suitable for the determination of the hemoglobin derivative such as $HbA_{1c}$. As described above it is possible to produce polyclonal and monoclonal antibodies against hemoglobin derivatives, preferably $HbA_{1c}$, which specifically bind the characteristic epitopes of the hemoglobin derivatives (U.S. Pat. No. 4,247,533, EP-A-0 316 306 and EP-A-0 201 187).

The immunological test variant, the type of label as well as the method of detecting the measurement signals are known methods of the state of the art. Direct or indirect (competitive) test procedures, e.g. sandwich tests with enzyme labels (ELISA), IEMA test procedures, RIAs, precipitation and agglutination tests and homogeneous immunoassays such as the CEDIA®, EMIT or FPIA technology are suitable.

In the wet test the immunological determination of the hemoglobin derivative is preferably carried out according to the TINIA (turbidimetric inhibition immunoassay) technique since a separation step is not necessary in this case. An analyte-specific antibody and a polyhapten agglutinizing agent are added to the sample. The polyhapten consists of a carrier material e.g. albumin, dextran or IgG, to which several epitopes i.e. glycosylated peptides are coupled which the specific antibodies can bind. Since the precipitation of the antibodies can only take place via the polyhapten, an increase in turbidity which can be determined nephelometrically or turbidimetrically, is obtained with decreasing contents of analyte in the sample.

The hemoglobin derivative-specific antibody is preferably already present in the reaction buffer. After addition of the reaction buffer, the total hemoglobin content in the resulting mixture can at first be determined photometrically. The precipitation reaction is started by addition of a solution which contains the polyhapten. After a short incubation period, for which 5 minutes is usually adequate, the resulting turbidity is measured at a suitable wavelength, preferably at wavelengths of 340 to 600 nm, 340 nm being particularly preferred and the hemoglobin derivative concentration is determined from this. Since the measurement of total hemoglobin is carried out at wavelengths of 500 to 650 nm, preferably at 546 or 570 nm, the two measurements do not interfere with each other and can therefore be carried out consecutively in one cuvette in the same reaction solution.

When preparing the polyhapten solution, i.e. the liquid galenic form of the polyhapten i.e. a carrier material to which several glycosylated peptides are coupled, it turned out that this is not stable in the phosphate buffer which is usually used at a pH of 7.0–7.5 and can lead to a decomposition of the glycoprotein during longer storage. Such instabilities of glycosylated proteins in phosphate buffer are for example known from Ahmed et al., J. Biol. Chem. 261 (1986), 4889–4894. Stabilization of the glycosylated polyhapten was achieved by using a MES buffer at a concentration of 5 to 200 mmol/l, preferably 20–50 mmol/l and a pH of 5.0–8.0, preferably between 6.0 to 6.5, and by the simultaneous addition of EDTA or of an equivalent complexing agent at a preferred concentration of 1–50 mmol/l one of 0.1–20 mmol/l being particularly preferred. Addition of bovine serum albumin (BSA) at a preferred concentration of 0.1–2%, preferably 1%, had a further positive effect on the stability of the polyhapten solution. This polyhapten solution can be stored for more than 12 months at 4° C. without observing significant instabilities of the polyhapten or glycosylated proteins or peptides. When stressed for 3 weeks at 35° C., decreases in signal of only 15–20% of the original absorbance signal occur. This stabilization of the glycosylated polyhapten is also applicaple to solutions of glycosylated peptides and glycosylated proteins.

The immunological determination of the hemoglobin derivative as a dry test is preferably carried out according to the IEMA test technique. After addition of the reaction buffer to the hemolyzed blood sample the specific enzyme-labelled antibody is added. In a preferred embodiment the antibody is already present in the reaction buffer. After a short incubation the mixture is applied to a test carrier. The free enzyme-labelled antibodies are captured on an epitope matrix i.e. a test carrier zone to which several epitopes to which the specific antibodies can bind are coupled. In a further zone, i.e. the test zone, the complex of the hemoglobin derivative and the labelled antibody is determined by reflectance photometry by conversion of a suitable enzyme substrate. The substrate can be present in the test zone or gain access thereto by bringing the test zone into contact with a further zone which contains the substrate.

It is contemplated to prepare a test kit which, in addition to the hemolysis reagent contains, the other reagents in a dissolved or lyophilized form or applied to a test carrier in at least two separate packages.

The present invention is elucidated by the following examples:

EXAMPLE 1

Simultaneous Determination of Total Hemoglobin and HbA1c in a Wet Test

The experiments were carried out on a Hitachi 717 of the Boehringer Mannheim GmbH. The total hemoglobin content was measured photometrically at a wavelength of 546 nm. The immunological detection of $HbA_{1c}$ was carried out by turbidimetric measurement at 340 nm according to the TINIA test technique. All determinations and incubations were carried out at a temperature of 37° C.

The following solutions were used:

Hemolysis Reagent

| | |
|---|---|
| 20 mM | sodium phosphate buffer, pH 7.0 |
| 1.0% | SDS |
| 0.1% | sodium azide |
| 0.02% | potassium hexacyanoferrate (III) |
| 0.5% | Brij 35 |

Reaction Buffer

| | |
|---|---|
| 20 mM | MES buffer pH 6.0 |
| 150 mM | sodium chloride |
| 3.0% | PEG 6000 |
| 0.5% | Brij 35 |
| 0.1% | bovine serum albumin |
| 0.1% | sodium azide |
| 10 mM | EDTA |
| 6 mg/ml | PAB <$HbA_{1c}$> S-IgG (DE) (polyclonal sheep AB against $HbA_{1c}$) or |
| 100 µg/ml | MAB <$HbA_{1c}$> M-IgG (DE) (monoclonal mouse AB against $HbA_{1c}$) |

Polyhapten Solution

| | |
|---|---|
| 20 mM | MES buffer pH 6.0 |
| 150 mM | sodium chloride |
| 6.0% | PEG 6000 |
| 0.5% | Brij 35 |
| 0.1% | bovine serum albumin |
| 25 μg/ml | polyhapten $HbA_{1c}$-β-1-4(cys, MHS)-BSA 18:1 |

The hemolysis reagent was added to the blood sample in a ratio of 100:1 and incubated for 2 minutes at 25° C. 250 μl reaction buffer was added to 5 μl hemolyzed sample. After 4 minutes the absorbance of the total hemoglobin was measured at 546 nm (A1). The absorbance at 340 nm (A2) was measured one minute later and subsequently 50 μl polyhapten solution was added by pipette and incubated for 5 minutes. Afterwards the turbidity was measured at 340 nm (A3).

In order to determine the $HbA_{1c}$ value in g/dl, the absorbance difference $\Delta A = A3 - k \cdot A2$ is plotted against the $HbA_{1c}$ concentration and determined graphically.

$$k = \text{volume correction factor} = \frac{\text{volume sample} + \text{volume reaction buffer}}{\text{total volume}}$$

The concentration of the total hemoglobin is calculated from a constant factor K by multiplication with A1 (K=molar extinction coefficient of the hemoglobin chromophore× dilution factor). EDTA whole blood with a known hemoglobin and $HbA_{1c}$ content served as a calibrator. The EDTA whole blood was diluted with different amounts of hemolysis reagent in order to establish a calibration curve.

Figure 1:
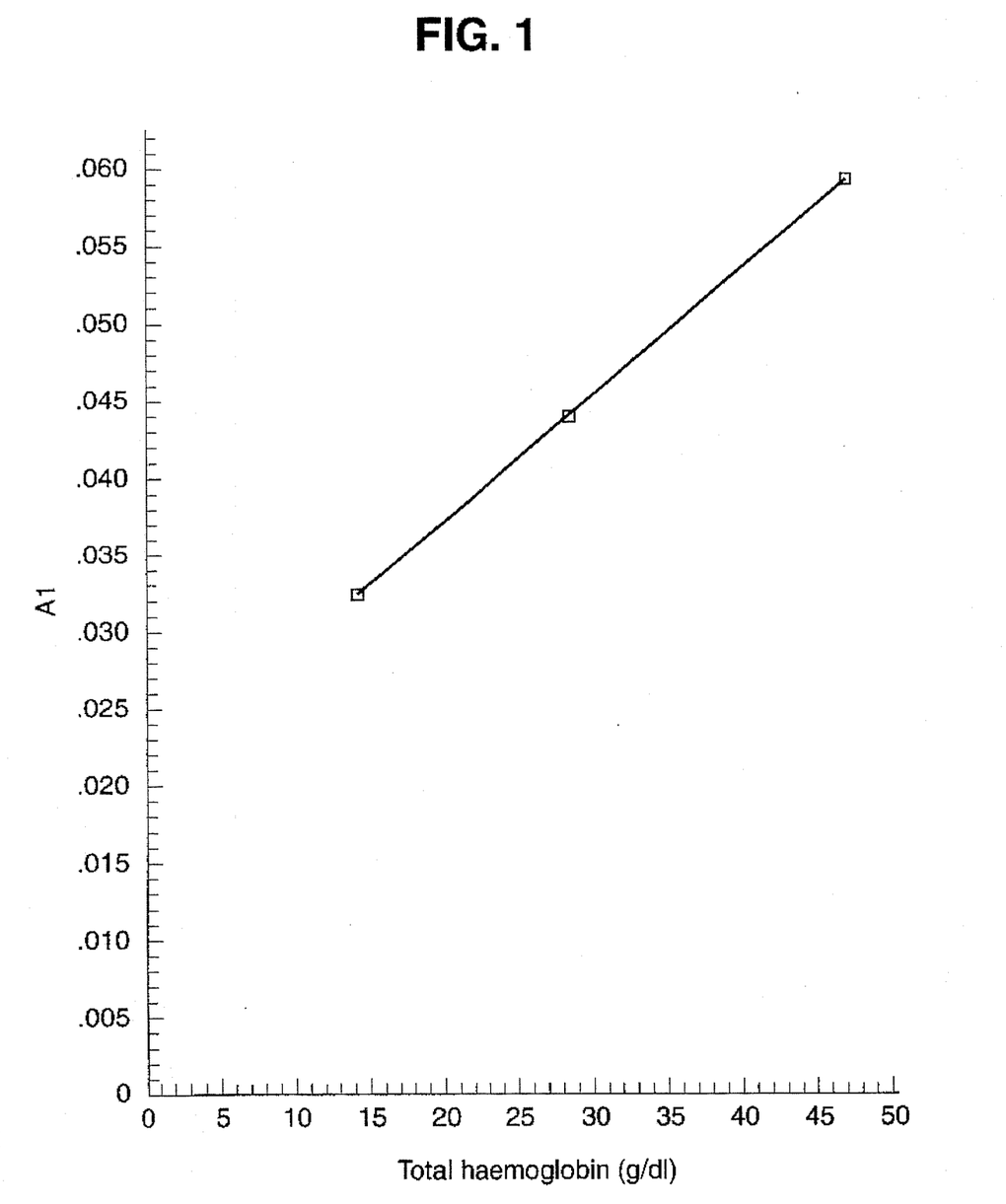
FIG. 1 shows graphically, a plot of varying hemoglobin content measured at 546 nm.
Figure 2:
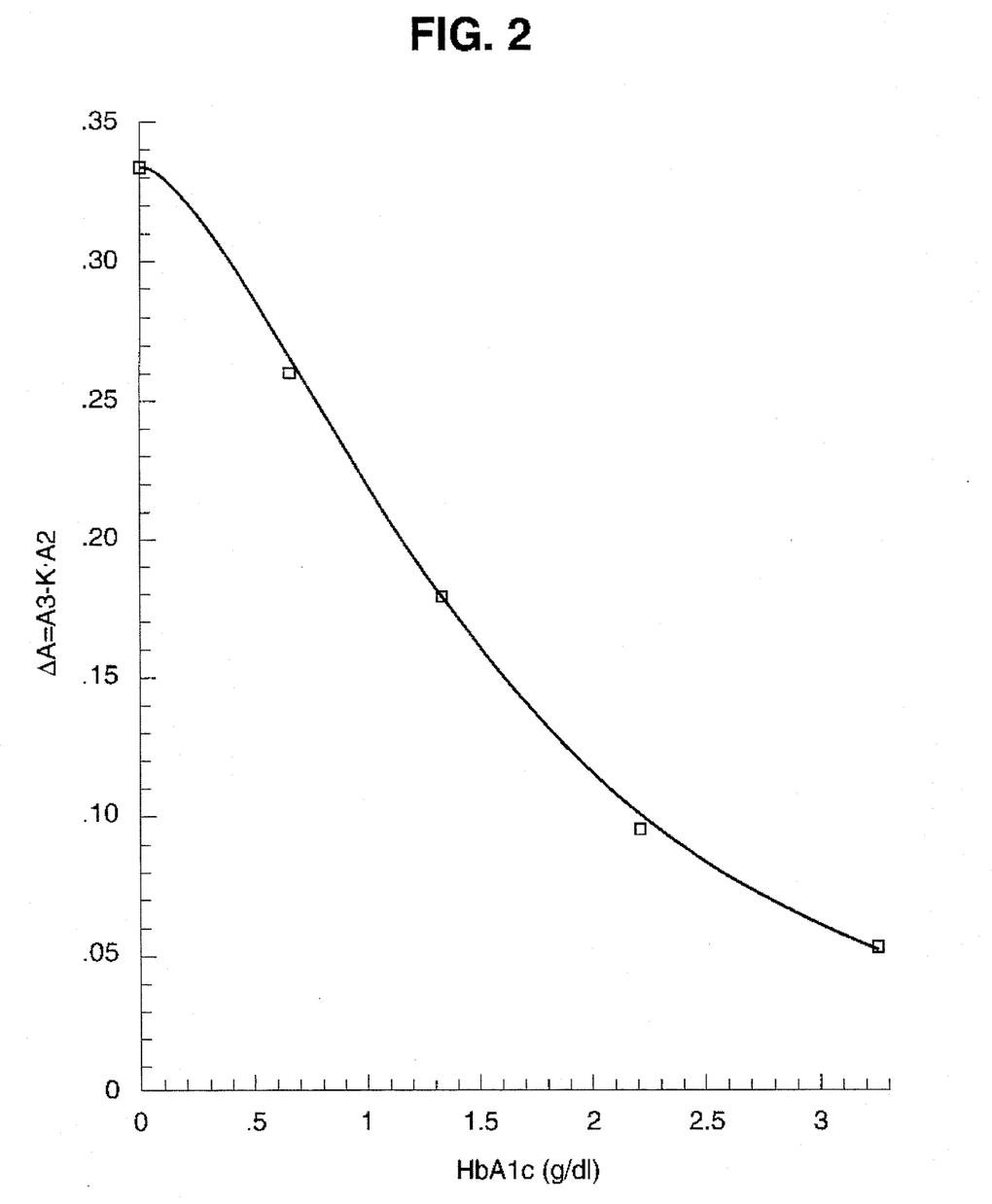
FIG. 2 depicts a calibration curve for determining glycated hemoglobin at 546 nm.

The calibration curves are shown diagrammatically in FIGS. 1 and 2. In FIG. 1 the total hemoglobin concentration was plotted against A1. It yields a linear relation. Thus it is possible to multiply with a constant factor in the calculation. In FIG. 2 the absorbance difference $\Delta A = A3 - k \cdot A2$ is plotted against the $HbA_{1c}$ content.

Figure 3:
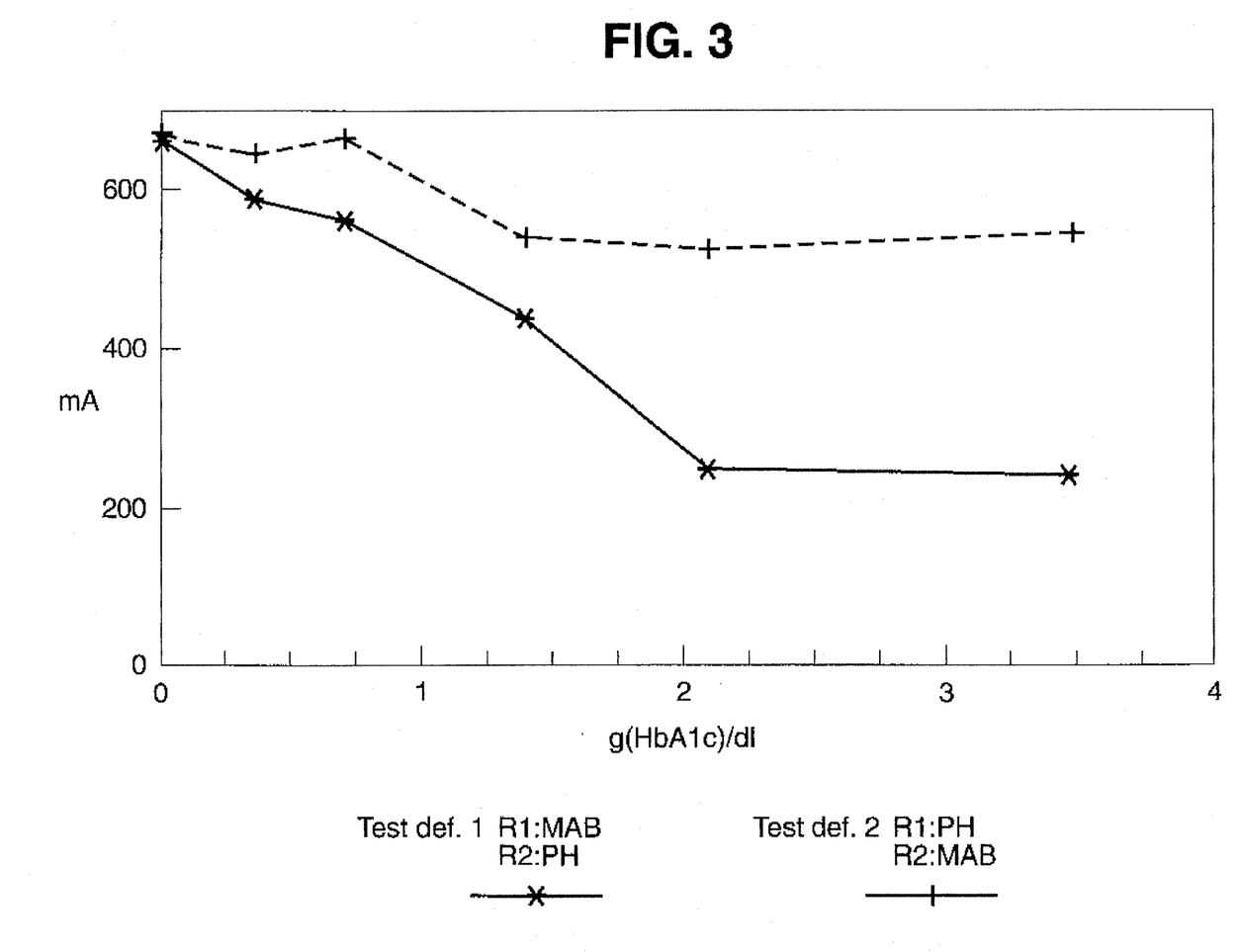
FIG. 3 shows a comparison of sensitivities for determining glycated hemoglobin where the order of addition of reagents (antibody and polyhapten) is varied.

In further experiments the polyhapten solution was added first to the hemolyzed blood sample by pipette and after a 5 minute incubation the precipitation reaction was started by addition of the reaction buffer which contains the specific antibody. This pipetting sequence led to a significantly lower sensitivity in the $HbA_{1c}$ determination (FIG. 3) compared to the pipetting sequence mentioned above in which the antibody was added first and the polyhapten was added subsequently.

EXAMPLE 2

Test Strips for the Determination of Total Hemoglobin and HbA1c

300 μl hemolysis reagent was added to 30 μl whole blood and incubated for 10 minutes at 20° C. The hemolysis reagent consisted of a 0.18% SDS solution which was buffered at pH 7.

Figure 4:
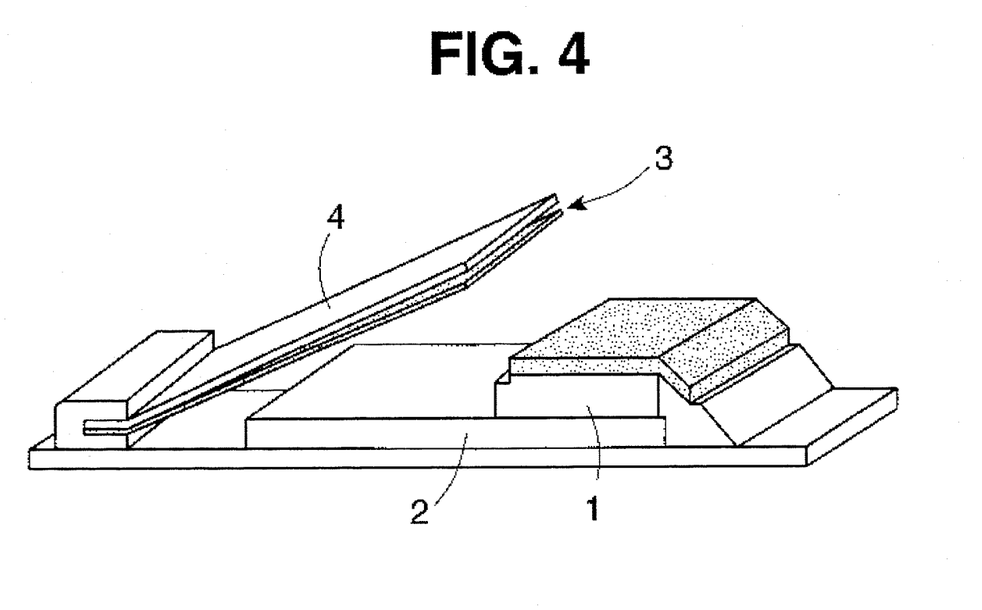
FIG. 4 shows a test strip which can be used to carry out the assays of the invention.

In order to determine total hemoglobin, 32 μl of the hemolyzed blood sample was applied to a test strip. The structure of the test strip is shown diagrammatically in FIG. 4. It merely consists of an untreated glass fibre dosage pad (1), an untreated glass fibre transport pad (2), an untreated polyester fabric (3) and a transparent polycarbonate foil (4). The test strip contains no additional chemicals. Using this experimental procedure, the total hemoglobin content of the blood sample can be measured very precisely at a wavelength of 576 nm.

Variation coefficients below 2.5% were obtained (Table 1).

TABLE 1

Determination of total hemoglobin
The CV was calculated in each case from 10 single measurements.

| Hb concentration [g/dl] | CV [%] |
|---|---|
| 14.1 | 1.0 |
| 17.5 | 2.5 |
| 13.7 | 1.9 |
| 14.7 | 1.8 |

Figure 5:
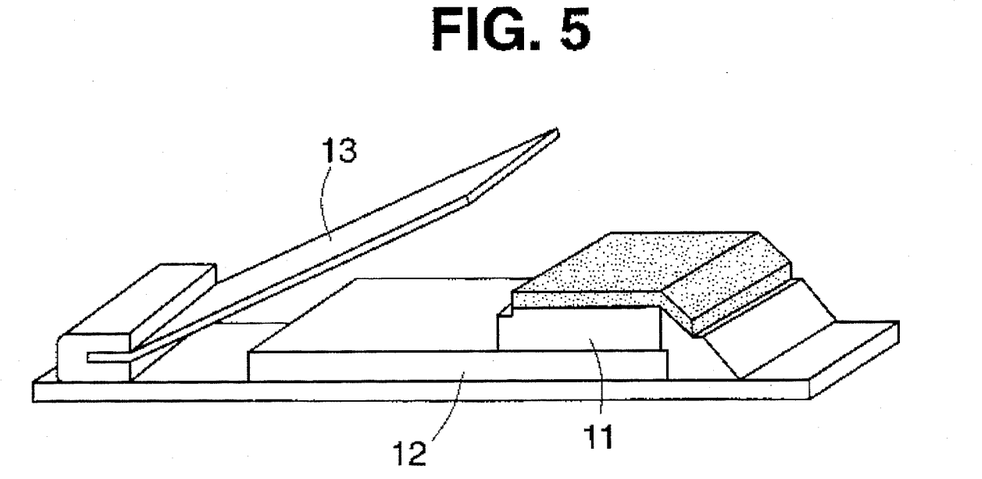
FIG. 5 depicts another test strip which can be used to carry out the assay of the invention.

In order to determine the $HbA_{1c}$ concentration, 1200 μl reaction buffer is added to 32 μl of the hemolyzed sample and incubated for 10 minutes. The reaction buffer consists of 100 mM Hepes, pH 7.4, 100 mM NaCl and 0.1% Brij 35 with the MAB-enzyme conjugate. 32 μl of the mixture is applied to the test strip which is shown diagrammatically in FIG. 5. Free antibody-enzyme conjugate is captured on an epitope matrix (11). In the adjacent zone, the transport pad (12), the $HbA_{1c}$ antibody-enzyme complex is determined by reflectance photometry by reaction of the substrate after the substrate pad (13) which contains the substrate is brought into contact with the transport pad (12) (Table 2).

TABLE 2

Determination of the $HbA_{1c}$ concentration by means of a test strip
The CV was determined in each case from 10 single measurements.

| $HbA_{1c}$ concentration [g/dl] | CV [%] |
|---|---|
| 0.8 | 6.8 |
| 1.1 | 5.4 |
| 1.4 | 6.0 |

EXAMPLE 3

Influence of Various Ionic Detergents on the Determination of HbA1c

The experiments were carried out as described in example 1. The hemolysis reagent had the following composition:

| | |
|---|---|
| 20 mM | sodium phosphate buffer, pH 7.2 |
| 0.1% | sodium azide |
| 0.02% | potassium hexacyanoferrate (III) |
| 0.5% | Brij 35 |

The ionic detergents listed in Table 3 were present in the respective concentrations stated there.

In the case of TTAB and CTAB no potassium hexacyanoferrate (III) was included in the hemolysis reagent since this precipitates with these detergents.

The composition of the reaction buffer and of the polyhapten solution corresponds to example 1.

A standard with a $HbA_{1c}$ content of 3.2 g/dl was used as the blood sample. All ionic detergents which were tested resulted in lysis of the cells and epitope release. The anionic detergent SDS and the cationic detergents TTAB and CTAB proved to be the most suitable.

TABLE 3

HbA$_{1c}$ determination
Influence of various ionic detergents in the hemolysis reagent.
The absorbance was measured at 340 nm

| Detergent | Concentration in the hemolysis reagent | A1 [0 g/dl HbA$_{1c}$] | A1 [3.2 g/dl HbA$_{1c}$] | ΔA = A1 − A2 |
|---|---|---|---|---|
| SDS | 0.5% | 337 mA | 73 mA | 264 mA |
| SDS | 1.0% | 338 mA | 80 mA | 258 mA |
| Zwittergent 3-14 | 0.5% | 341 mA | 172 mA | 169 mA |
| Zwittergent 3-14 | 1.0% | 343 mA | 139 mA | 204 mA |
| TTAB | 1.0% | 377 mA | 149 mA | 228 mA |
| CTAB | 1.0% | 374 mA | 137 mA | 237 mA |
| Control without ionic detergent | — | 340 mA | 275 mA | 65 mA |

EXAMPLE 4

Dependence of the Dynamic Measurement Range of the HbA1c Determination on the Brij 35 Concentration The experiments were carried out as in example 3. 1% SDS was used constantly in the hemolysis reagent. The concentration of Brij 35 in the reaction buffer was varied within the range stated in Table 4. The HbA$_{1c}$ standard mentioned in example 3 served as the sample.

The measurement range already increased from 47 mA for the control to 233 mA by addition of 0.1% Brij 35. The preferred concentration of Brij 35 was 0.1 to 1.0%.

TABLE 4

Influence of various Brij concentrations in the reaction buffer on the HbA$_{1c}$ determination
The absorbance was measured at 340 nm

| Concentration of Brij 35 in the reaction buffer | A1 [0 g/dl HbA$_{1c}$] | A2 [3.2 g/dl HbA$_{1c}$] | ΔA = A1 − A2 |
|---|---|---|---|
| — | 240 mA | 193 mA | 47 mA |
| 0.1% | 266 mA | 33 mA | 233 mA |
| 0.25% | 274 mA | 40 mA | 234 mA |
| 0.5% | 302 mA | 57 mA | 245 mA |
| 1.0% | 351 mA | 99 mA | 252 mA |
| 2.0% | 385 mA | 242 mA | 143 mA |

EXAMPLE 5

Influence of Various Detergents in the Reaction Buffer on the HbA1c Determination The experiments were carried out analogously to example 4. The detergents stated in Table 5 were used in the reaction buffer. The dynamic measurement range was extended most by addition of Brij 35, 56 and 58 as well as Myrj 52 and 59. However, other non-ionic detergents such as Triton and zwitterionic detergents such as Zwittergent 3-14 also showed a substantial positive effect compared to the control.

TABLE 5

Influence of detergents in the reaction buffer

| Detergent | Concentration in the reaction buffer | A1 [0 g/dl HbA$_{1c}$] | A1 [3.2 g/dl HbA$_{1c}$] | ΔA = A1 − A2 |
|---|---|---|---|---|
| Control | — | 240 mA | 193 mA | 47 mA |
| Brij 35 | 0.5% | 302 mA | 57 mA | 245 mA |
| Brij 56 | 0.5% | 302 mA | 57 mA | 245 mA |
| Brij 58 | 0.5% | 303 mA | 51 mA | 252 mA |
| TritonX114 | 0.2% | 523 mA | 275 mA | 248 mA |
| TritonX100 | 0.5% | 298 mA | 202 mA | 96 mA |
| Tween 80 | 0.25% | 277 mA | 143 mA | 134 mA |
| Tween 60 | 0.25% | 266 mA | 75 mA | 191 mA |
| Tween 40 | 0.25% | 276 mA | 86 mA | 189 mA |
| Tween 20 | 0.1% | 266 mA | 131 mA | 135 mA |
| Zwittergent 3-14 | 0.1% | 308 mA | 155 mA | 153 mA |
| Myrj 52 | 0.5% | 308 mA | 40 mA | 268 mA |
| Myrj 59 | 0.5% | 317 mA | 31 mA | 286 mA |

EXAMPLE 6

Simultaneous Determination of Total Hemoglobin and HbA1c with the Specific Brown-green Hemoglobin Chromophore The experiments were carried out on a Hitachi 717 of the Boehringer Mannheim GmbH. The total hemoglobin content was measured photometrically at a wavelength of 570 nm. The immunological determination of HbA$_{1c}$ was carried out according to the TINIA test technique by turbidimetric measurement at 340 nm. All determinations and incubations were carried out at a temperature of 37° C.

The following solutions were used:

Hemolysis Reagent

| | |
|---|---|
| 20 mM | sodium phosphate buffer pH 7.4 |
| 1.0% | tetradecyltrimethylammonium bromide (TTAB) |
| 0.01% | methylisothiazolone |
| 0.02% | Bronidox ® K |
| 0.5% | Brij 35 |
| 10 mM | EDTA |

Reaction Buffer

| | |
|---|---|
| 20 mM | MES buffer pH 6.0 |
| 150 mM | sodium chloride |
| 3.0% | PEG 6000 |
| 0.5% | Brij 35 |
| 0.01% | methylisothiazolone |
| 0.02% | Bronidox ® K |
| 1.2 mg/ml | PAK <HbA$_{1c}$> S-IgG (DE) (polyclonal sheep AB against HbA$_{1c}$) |

Polyhapten Solution

| | |
|---|---|
| 20 mM | MES buffer pH 6.0 |
| 150 mM | sodium chloride |
| 6.0% | PEG 6000 |
| 0.5% | Brij 35 |
| 20 μg/ml | polyhapten |

The hemolysis reagent was added to the blood sample in a ratio of 100:1 and incubated for 2 minutes at 25° C. 250 μl reaction buffer was added to 10 μl hemolyzed sample. After 4 minutes the absorbance of the total hemoglobin was measured at 570 nm (A1). One minute later the absorbance was measured at 340 nm (A2) and subsequently 50 μl polyhapten solution was added by pipette and incubated for five minutes. Afterwards the turbidity is measured at 340 nm (A3).

In order to determine the $HbA_{1c}$ value in g/dl, the difference in absorbance $\Delta A = A3 - k \cdot A2$ is plotted against the $HbA_{1c}$ concentration and determined graphically.

$$k = \text{volume correction factor} = \frac{\text{volume sample} + \text{volume reaction buffer}}{\text{total volume}}$$

Figure 6:
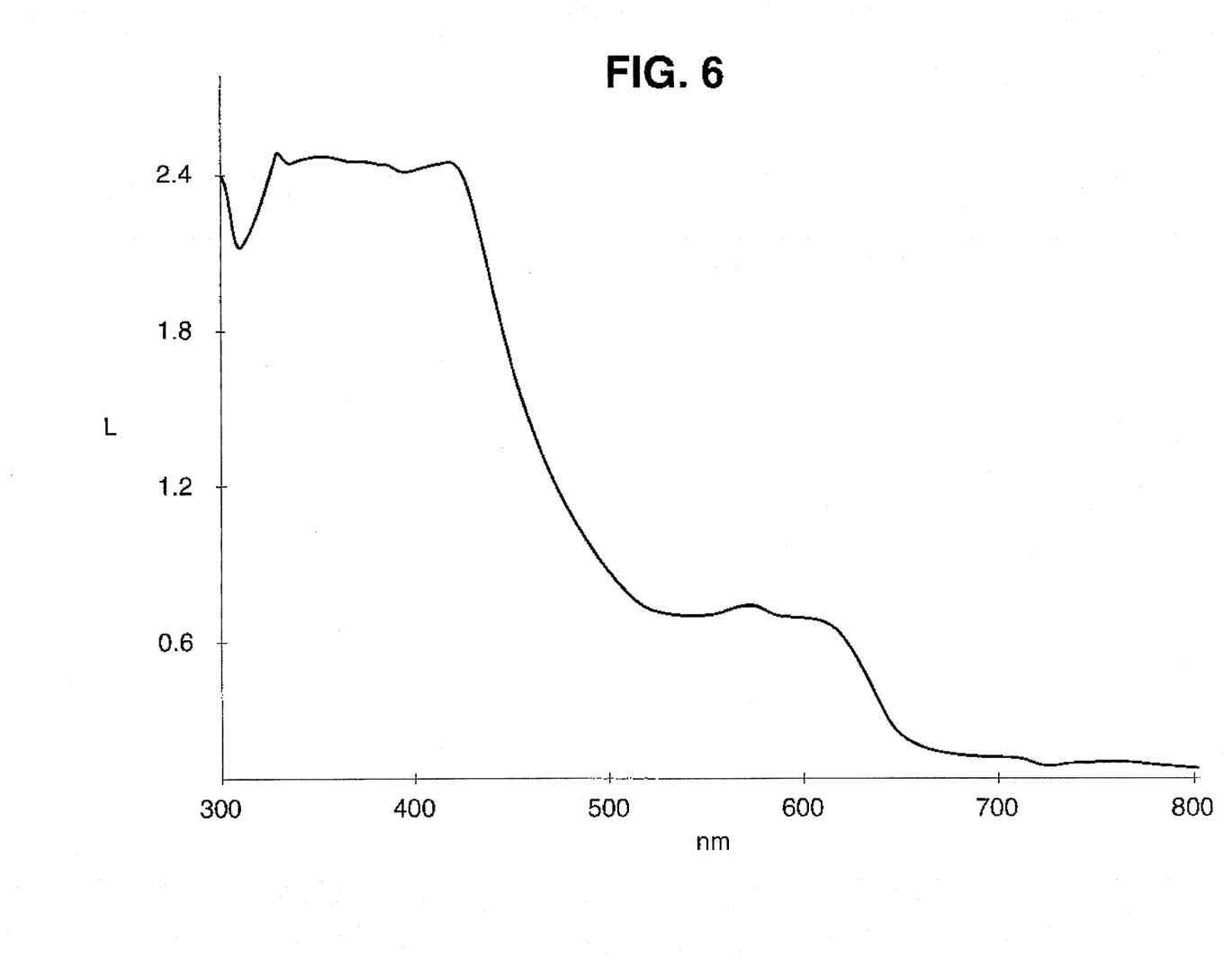
FIG. 6 displays the absorbance spectra of the "brown-green" hemoglobin chromophore.

The concentration of the total hemoglobin is calculated from a constant factor K by multiplying with A1 (K=molar extinction coefficient of the hemoglobin chromophore×dilution factor). The characteristic absorbance spectrum is shown in FIG. 6. EDTA-whole blood with a known hemoglobin and $HbA_{1c}$ content served as the calibrator. The EDTA-whole blood was diluted with different amounts of hemolysis reagent in order to establish a calibration curve.

Figure 7:
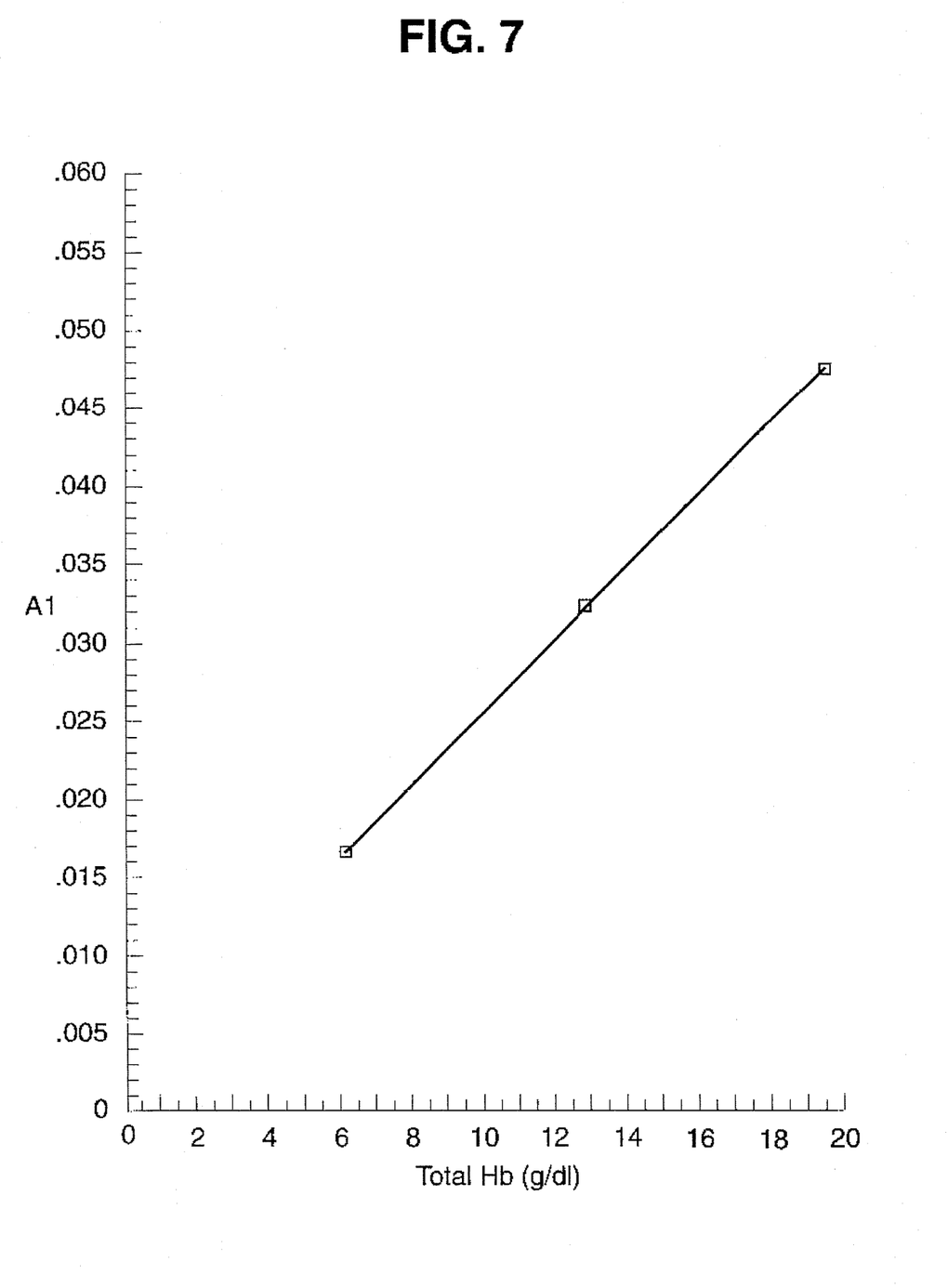
FIG. 7 displays the total hemoglobin calibration curve of the brown-green hemoglobin chromophore.
Figure 8:
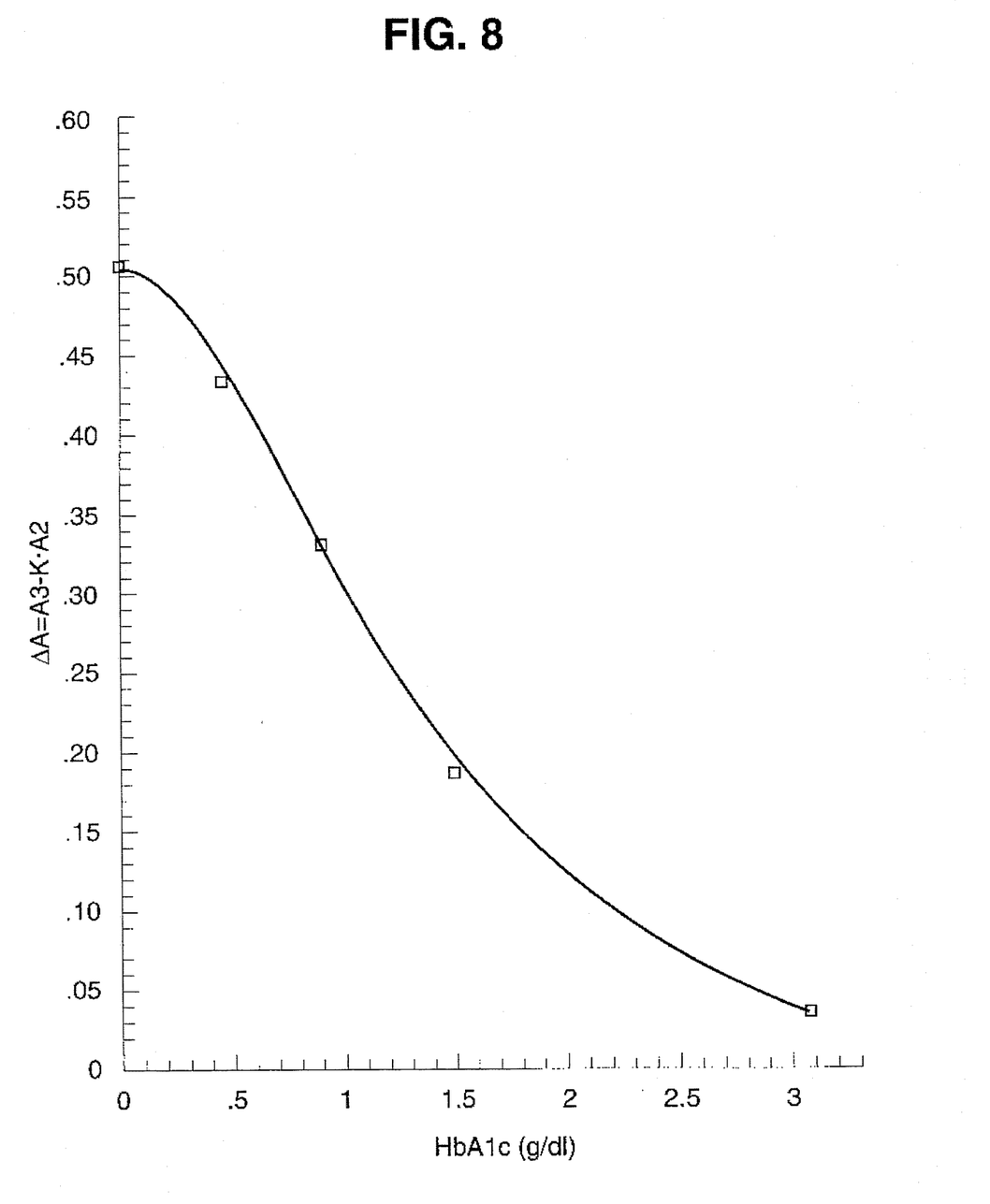
FIG. 8 displays the HbA1c calibration curve of the brown-green hemoglobin chromophore.

The calibration curves are shown graphically in FIGS. 7 and 8. In FIG. 7 the total hemoglobin concentration was plotted against A1. It yields a linear relation. Thus one can multiply with a constant factor K in the calculation. In FIG. 8 the difference in absorbance $\Delta A = A3 - k \cdot A2$ was plotted against the $HbA_{1c}$ content.

We claim:

1. Method for immunologically determining glycated hemoglobin in blood, comprising:
   (a) treating a blood sample which contains said glycated hemoglobin with a hemolysis reagent consisting essentially of an ionic detergent which has a pH of from 5.5 to 9.5, for a period of no more than 10 minutes, at a temperature of from 4° C. to 37° C., to hemolyze said blood sample,
   (b) contacting the hemolyzed blood sample with at least one immune reagent which specifically binds to glycated hemoglobin, and
   (c) determining binding of said immune reagent as a determination of glycated hemoglobin in said blood sample.

2. Method for immunologically determining glycated hemoglobin in blood, comprising:
   (a) treating a blood sample which contains glycated hemoglobin with a hemolysis reagent consisting essentially of an ionic detergent which has a pH of from 5 to 9.5, for a period of no more than 10 minutes, at a temperature of from 4° C. to 37° C., to hemolyze said blood sample,
   (b) contacting said hemolyzed blood sample with (i) a first immune reactant which specifically binds to glycated hemoglobin and (ii) a second immune reactant which binds to said first immune reactant, and
   (c) determining binding of said first immune reactant to said second immune reactant as a determination of glycated hemoglobin in said blood sample.

3. Method for immunologically determining glycated hemoglobin in blood, comprising:
   (a) treating a blood sample which contains glycated hemoglobin with a hemolysis reagent consisting essentially of a mixture of an ionic detergent and a non-ionic detergent, said mixture having a pH of from 5.0 to 9.5, for a period of no more than 10 minutes, a temperature of from 4° C. to 37° C. to hemolyze said blood sample,
   (b) contacting said hemolyzed blood sample with at least one immune reactant which specifically binds to glycated hemoglobin, and
   (c) determining binding of said immune reactant as a determination of glycated hemoglobin in said blood sample.

4. Method for immunologically determining glycated hemoglobin in a blood sample, comprising:
   (a) treating a blood sample which contains glycated hemoglobin with a hemolysis reagent consisting essentially of a mixture of an ionic detergent and a non-ionic detergent, wherein said mixture has a pH of from 5.0 to 9.5, for a period of no more than 10 minutes, at a temperature of from 4° C. to 37° C. to hemolyze said blood sample,
   (b) contacting said hemolyzed blood sample with (i) a first immune reactant which specifically binds to glycated hemoglobin and (ii) a second immune reactant which binds to said first immune reactant, and
   (c) determining said binding as a determination of glycated hemoglobin in said blood sample.

5. The method of claim 1, 2, 3 or 4, further comprising contacting said hemolyzed blood sample with a buffer which contains a non-ionic or zwitterionic detergent prior to determining binding of said first immune reactant to said hemoglobin derivative.

6. The method of claim 5, wherein said buffer contains said first immune reactant.

7. The method of claim 1, 2, 3 or 4, wherein said glycated hemoglobin is $HbA_{1c}$.

8. The method of claim 1, 2, 3 or 4, further comprising determining total hemoglobin content in said hemolyzed blood sample chromophorically.

9. The method of claim 3 or 4, comprises treating said sample for two minutes or less.

10. The method of claim 3 or 4, comprising incubating said sample at room temperature.

11. The method of claim 1, 2, 3 or 4, wherein said ionic detergent is sodium dodecylsulfate, sodium dioctylsulfocuccinate, tetradecyltrimethyl ammonium bromide, or cetyltrimethyl ammonium bromide.

12. The method of claim 1, 2, 3 or 4, wherein said hemolysis reagent contains a buffer.

13. The method of claim 1, 2, 3 or 4, wherein said hemolysis reagent contains an oxidizing agent.

* * * * *